United States Patent
White et al.

(10) Patent No.: US 7,754,145 B2
(45) Date of Patent: *Jul. 13, 2010

(54) FLUORPHORE EMBEDDED/INCORPORATING/BRIDGED PERIODIC MESOPOROUS ORGANOSILICAS AS RECOGNITION PHOTO-DECONTAMINATION CATALYSTS

(75) Inventors: Brandy J White, Alexandria, VA (US); Mazyar Zeinali, Columbia, MA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 702 days.

This patent is subject to a terminal disclaimer.

(21) Appl. No.: 11/465,355

(22) Filed: Aug. 17, 2006

(65) Prior Publication Data

US 2007/0073095 A1    Mar. 29, 2007

Related U.S. Application Data

(60) Provisional application No. 60/708,912, filed on Aug. 17, 2005.

(51) Int. Cl.
*G01N 33/00* (2006.01)
(52) U.S. Cl. .................. 422/57; 422/55; 422/56; 422/68.1; 422/82.05; 422/82.06; 422/82.07; 422/82.08
(58) Field of Classification Search .......... 422/555, 422/56, 57, 68.1, 82.05, 82.06, 82.07, 82.08, 422/83, 55
See application file for complete search history.

(56) References Cited

U.S. PATENT DOCUMENTS

| 6,028,025 | A | * | 2/2000 | Ying et al. ............... 502/171 |
| 6,310,110 | B1 | | 10/2001 | Markowitz et al. |
| 6,583,191 | B2 | | 6/2003 | Markowitz et al. |
| 6,660,780 | B2 | | 12/2003 | Markowitz et al. |
| 6,673,246 | B2 | | 1/2004 | Markowitz et al. |
| 6,713,416 | B2 | | 3/2004 | Markowitz et al. |

OTHER PUBLICATIONS

Umar, "Self-assembled monolayer of copper(II) meso-tetra(4-sulfanatophyenyl) porphyrin as an optical gas sensor" Sensors and Actuators B101 (Apr. 27, 2004) pp. 231-235.*
Wahab "Periodic Mesoporous Organosilica materials incorporating various organic functional groups: Synthesis, structural characterization and morphology" Chem. Material. published Mar. 17, 2005, 17, pp. 2165-2174.*
Inagaki et al., Novel Mesoporous Materials with a Uniform Distribution of Organic Groups and Inorganic Oxide in Their Framewokrs, J. Am. Chem. Soc. 1999, 121,9611.

(Continued)

*Primary Examiner*—Sam P Siefke
(74) *Attorney, Agent, or Firm*—Amy Ressing

(57) ABSTRACT

Provided photo-decontamination catalyst material comprising an optically active molecule embedded/incorporated/bridged in a periodic mesoporous organosilica (PMO). The optically active molecule is a typically a fluorophore or chromophore, more specifically, a porphyrin or phthalocyanine. The periodic mesoporous organosilica can be a template directed molecularly imprinted periodic mesoporous organosilica. The PMO material incorporating an optically active molecule is useful as a catalyst in photo-decontamination applications, as well as a detection element for stand-off point detection system.

16 Claims, 5 Drawing Sheets

OTHER PUBLICATIONS

Asefa et al., Periodic mesoporous organosilicas with organic groups inside the channel walls, Nature 1999. 402, 867.

Melde et al., Mesoporous Sieves with Unified Hybrid Inorganic/Organic Frameworks, Chem. Mater. 1999, 11, 3302.

Kreseg et al., Ordered mesoporous molecular sieves synthesized by a liquid-crystal template mechanism, Nature, 359. 710, Oct. 22, 1992.

Burleigh et al., Direct synthesis of periodic mesoporous organosilicas: Functional Incorporation by Co-Condensation with Organosilanes, J. Phys. Chem. B 2001, 105, 9935.

White, et al., Reagent-less detection of a competitive inhibitor of immobilized acetylcholinesterase, BiosenBioelec 2002, 17. 361.

White, et al., Enzyme-based detection of Sarin (GB) using planar waveguide absorbance spectroscopy, SensLett 2005. 3. 36.

White, et al., Competitive Inhibition of Cabonic Anhydrase by Water Soluble Porphyrins: Use of cabonic anhydrase as a $CO_2$ Sensor, SensLett 2005, 3, 59.

Burleigh, et al, Porous Polysilsesquioxanes for the Adsorption of Phenols, Environ Sci Technol. 36 (2002) 2515.

* cited by examiner

FLUORPHORE EMBEDDED/INCORPORATING/BRIDGED PERIODIC MESOPOROUS ORGANOSILICAS AS RECOGNITION PHOTO-DECONTAMINATION CATALYSTS

CROSS-REFERENCE TO RELATED APPLICATIONS

This Application is a Non-Prov of Prov (35 USC 119(e)) application 60/708,912 filed on Aug. 17, 2005, incorporated herein in full by reference. This application is related to N.C. 97,345, filed concurrent herewith, based on Prov (35 USC 119(e)) application 60/708,913, both incorporated herein in full by reference.

BACKGROUND OF THE INVENTION

Periodic mesoporous organosilicas (PMOs) are organic-inorganic polymers with highly ordered pore networks and large internal surface areas. They were first reported in 1999 (Inagaki et al., Mesoporous Materials with a Uniform Distribution of Organic Groups and Inorganic Oxide in Their Frameworks, J. Am. Chem. Soc. 1999, 121.9611; Asef et al., Periodic mesoporous organosilicas with organic groups inside the channel walls, Nature 1999, 402, 867; Melde et al., Mesoporous Sieves with Unified Hybrid Inorganic/Organic Frameworks, Chem. Mater. 1999, 11, 3302). These organosilicas were synthesized using a surfactant template approach (Kreseg et al., Ordered mesoporous molecular sieves synthesized by a liquid-crystal template mechanism, Nature, 359, 710, 22 Oct. 1992. Burleigh et al.. Direct synthesis of periodic mesoporous organosilicas: Functional Incorporation by Co-Condensation with Organosilanes, J. Phys. Chem. B 2001, 105, 9935) and have narrow pore size distributions with few blocked pores or obstructions commonly found in amorphous materials to impede molecular diffusion throughout their pore networks. PMOs possess structural rigidity arising from the siloxane groups and functionality due to the organic bridging group. In addition. specificity can be imparted to the PMOs via a template directed molecular imprinting process. Due to their structural stability, functionality, and specificity, the PMOs are very efficient sorbents for the removal, sequestration, and pre-concentration of pollutants and/or any targeted compound from both vapor and aqueous phase. Yet a secondary means, such as a spectroscopic or electrochemical technique, is required for the specific detection of the sorbate. The addition/embedding of molecules (ie molecular catalysts) would in effect add a catalytic capability to PMOs through the activity of the embedded molecule upon excitation.

Periodic mesoporous organosilicas (PMOs) provide organic functionality in a silica matrix through the combination of covalently linked organic and silica components. Material characteristics can be tuned for a particular application by changing the organic groups used as "bridges" in the silica matrix. The organic-inorganic polymers lend stability, selectivity and ease of modification to applications traditionally protein- or microorganism-based. Template directed molecular imprinting, employing a target-like compound, can be used to improve pore homogeneity and distribution and to enhance selectivity and binding characteristics. The use of a regenerable diethylbenzene-bridged PMO for the preferential adsorption of hydrocarbons over time scales on the order of minutes has been demonstrated previously. Other applications of PMOs include catalysis, filtration and/or purification, and chemical sensors. Decontamination applications involving PMO materials are based on adsorption of the contaminant onto the silicate, and not on degradation of the contaminant.

A porphyrin is a nearly flat molecule with a macrocycle of twenty carbon and four nitrogen atoms consisting of four pyrrole rings joined by methine bridges. The porphyrin macrocycle binds cyclic compounds cofacially even when the compound bears a nitrogen or the porphyrin has a metal coordinated to the central nitrogen atoms. They have been used as catalysts in a wide range of applications: degradation of chlorinated phenols, nitro-substituted toluene, and atrazine; oxidation of alkylaromatics; and oxidative cleavage of C—C bonds. When compared to proteins and microorganisms, porphyrins and metalloporphyrins are much less sensitive to variations in conditions such as temperature and pH than proteins and microorganisms and have been shown to withstanding temperatures above 150° C. The binding and catalytic characteristic of porphyrins can be altered through modification of the peripheral substituent groups or through incorporation of metals via coordination to the four central nitrogen atoms.

The molecular structure of the porphyrin consists of a large macrocycle around which a minimum of 22 $\pi$-electrons are shared. This large number of $\pi$-electrons results in a large extinction coefficient and spectral characteristics that are highly sensitive to changes in the environment of the molecule. Recent work (White, et al., Reagent-less detection of a competitive inhibitor of immobilized acetylcholinesterase, BiosenBioelec 2002, 17, 361, incorporated herein by reference) has shown that porphyrins can be used in conjunction with enzymes to achieve a higher degree of selectivity and allow for specific detection within a class of compounds only. The reversible, competitive inhibition of an enzyme by a porphyrin has been used for the detection, both in solution and vapor phase, of analytes such as organophosphates (including nerve agents/simulants) and carbon dioxide (White, et al., Enzyme-based detection of Sarin (GB) using planar waveguide absorbance spectroscopy, SensLett 2005, 3, 36 and White, et al., Competitive Inhibition of Cabonic Anhydrase by Water Soluble Porphyrins: Use of cabonic anhydrase as a CO2Sensor. SensLett 2005. 3, 59, both incorporated herein by reference).

The most well known example of porphyrin photocatalysis is photosynthesis in which the porphyrin is the central part of chlorophyll. Porphyrins have also been used as synthetic photocatalysts and are well know for generating reactive oxygen and nitrogen species. Porphyrin production of peroxides has also been demonstrated and this peroxide has been implicated in a Fenton-like cycle for the degradation of aromatic compounds. Evidence indicates the involvement of multiple pathways for the photocatalyzed degradation of aromatics by porphyrins including those involving activated water, reactive oxygen species, peroxides, and direct energy transfer.

BRIEF SUMMARY OF THE INVENTION

Disclosed is a photo-decontamination catalyst material comprising an optically active molecule embedded/incorporated/bridged in a periodic mesoporous organosilica (PMO). The optionally active molecule is a typically a fluorophore or chromophore, more specifically a porphyrin or phthalocyanine. The chromophores or fluorophores include, but are not limited to, fluorescein and fluorescein derivatives and analogues, indocyanine green, rhodamine, triphenylmethines, polymethines, cyanines, phalocyanines, naphthocyanines, merocyanines, lanthanide complexes or cryptates, fullerenes, oxatellurazoles, LaJolla blue, porphyrins and porphyrin analogues and natural chromophores/fluorophores such as chlorophyll, carotenoids, flavonoids, bilins, phytochrome, phycobilins, phycoerythrin, phycocyanines, retinoic acid and analogues such as retinoins and retinates. The periodic mesoporous organosilica can be a template directed molecularly imprinted periodic mesoporous organosilica.

The PMOs material incorporating an optically active molecule is useful as a catalyst in photo-decontamination applications, as well as a detection element for stand-off point detection system. The nanoporous organosilicas provide a degree of selectivity allowing for binding of compounds within a class for example, aromatics. The porphyrin-incorporating material disclosed here catalyzes the degradation of the contaminant using sunlight, allowing for reuse of the PMO material for repeated detection/decontamination applications.

DETAILED DESCRIPTION OF THE INVENTION

Combining the periodic mesoporous organosilica (PMOs) with the porphyrin achieves a semi-selective sensing element for the optical detection of cyclic organics and a material to catalyze the conversion of nitroaromatics when placed under sunlight illumination.

Photocatalyzed degradation to mineral of potentially harmful aromatics is possible using sunlight or other excitation source covering the blue to red regions of the visible spectrum owing to the ability of the nanoporous organosilicas to facilitate proper orientation of the fluorophore and analyte and to the capacity of porphyrins to catalyze reactions upon photo-excitation. Template directed molecular imprinted materials and processes that yield selective and higher capacity nanoporous organosilicas and their regeneration capability are disclosed in Markowitz et. al., U.S. Pat. No. 6,310,110, issued Oct. 30, 2001, Markowitz et. al., U.S. Pat. No. 6,583, 191, issued Jun. 24, 2003, Markowitz et. al., U.S. Pat. No. 6,660,780, issued Dec. 9, 2003, Markowitz et. al., U.S. Pat. No. 6,673,246, issued Jan. 6, 2004, and Markowitz et. al., U.S. Pat. No. 6,713,416, issued Mar. 30, 2004, all incorporated herein by reference.

Figure 1:
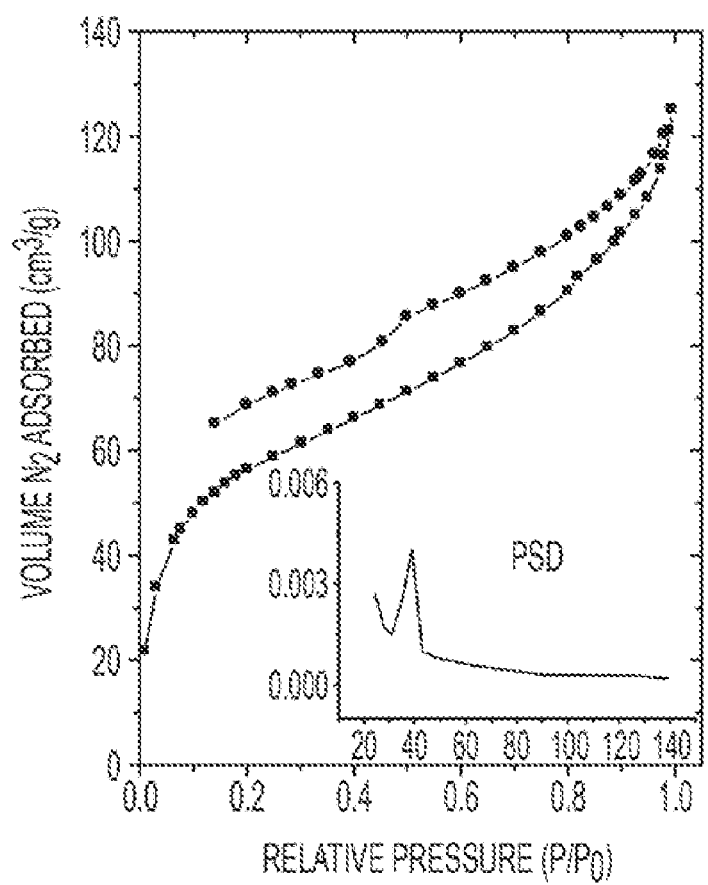
FIG. 1 shows the nitrogen sorption/desorption isotherms for IPDEB PMOs.

The synthesis of the porphyrin embedded molecularly imprinted PMO and the porphyrin embedded PMO is discussed in the example. The physiochemical properties of the PMOs are shown in Table 1. FIG. 1 shows the nitrogen sorption (■) and desorption (●) isotherms for IPDEB PMOs, demonstrating the creation of the porphyrin embedded PMO while maintaining porosity and with minimal reduction in surface area. The inset of plot shown in FIG. 1 shows the pore size distributions of the materials.

TABLE 1

| PMO | BET surface area $(m^2/g)$ | Total Pore Volume $(cm^3/g)$ | BJH Pore Diameter (Å) |
|---|---|---|---|
| IDEB | 244 | 0.19 | 31 |
| IPDEB | 206 | 0.18 | 34 |

Figure 2A:
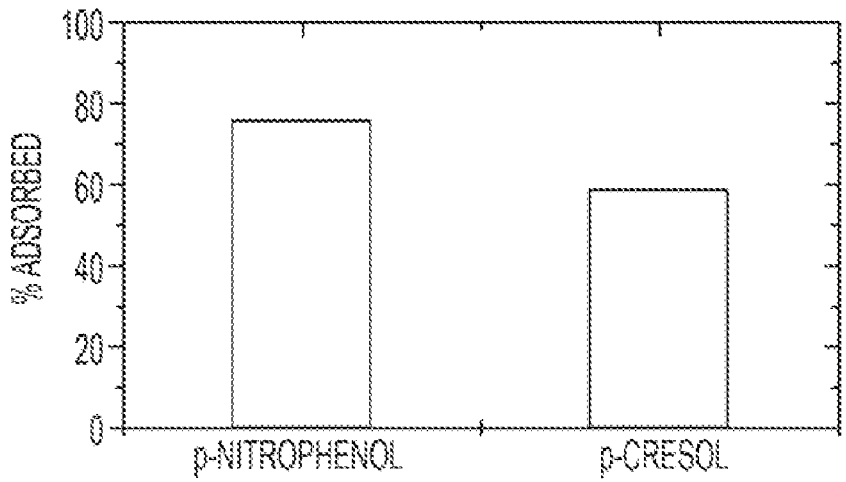
FIG. 2 shows the adsorption of p-nitrophenol and p-cresol from single sorbate and competitive binary solutions.
Figure 2B:
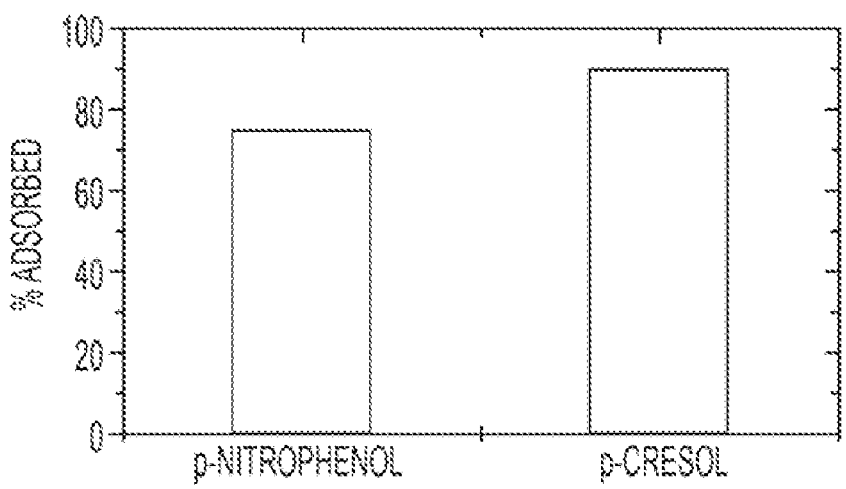

Adsorption of phenols onto porphyrin embedded molecularly imprinted PMO: The adsorption of p-nitrophenol and p-cresol from single sorbate and competitive binary solutions is shown in FIG. 2. As shown, the IPDEB PMO shows high affinity for substituted phenols from single sorbate (FIG. 2A) and binary (FIG. 2B); competitive p-nitrophenol-p-cresol) solution. FIG. 2 shows the adsorption of substituted phenols from single sorbate and competitive binary (p-nitrophenol-p-cresol) aqueous solution. 2.5 g/L of sorbent with 100 μM of either sorbate in single sorbate or 100 μM of each in binary solution.

Figure 3A:
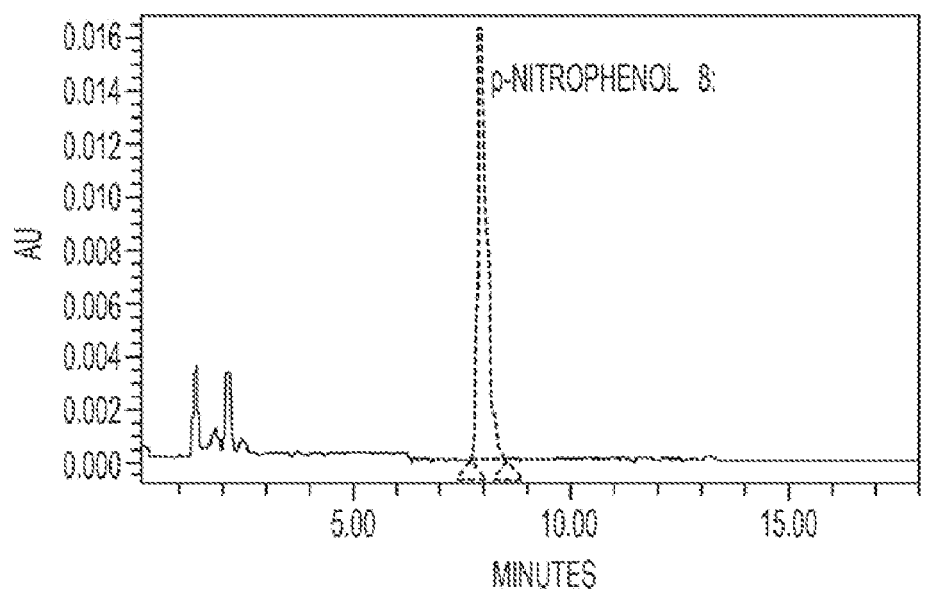
FIG. 3 shows the photodecontamination of p-nitrophenol.
Figure 3B:
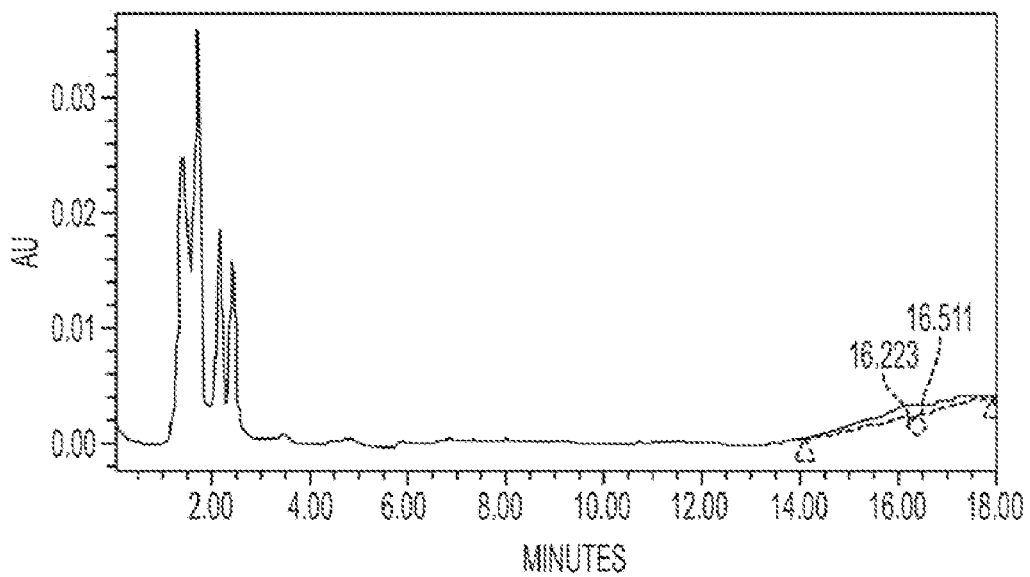

Photodecontamination of p-nitrophenol sorbed onto porphyrin embedded molecularly imprinted PMO. The photodecontamination of p-nitrophenol in solution in the presence of IDEB is demonstrated in FIG. 3. A solution containing p-nitrophenol was exposed to sunlight. No p-nitrophenol was detected in the solution after 18 hrs of exposure to sunlight (FIG. 3), compared to the solution that was not exposed to sunlight, where a significant amount of p-nitrophenol remained in solution. FIG. 3 shows the photodecontamination of p-nitrophenol. FIG. 3A shows the results when there was no exposure to sunlight. FIG. 3B shows the results after the solution was exposed to sunlight for 18 hrs.

The imprinted porphyrin embedded PMO described here is a high capacity, selective sorbent with the potential for use as a catalyst in photo-decontamination applications. The materials have the potential to provide the basis for a reactor type system for photo-decontamination applications either as the primary component or as a second stage filter.

The materials present effective photocatalysts through the combination of porphyrins with periodic mesoporous organosilicas. The porphyrin bound to the PMO materials is stabilized against the photo-degradation observed when it is sunlight illuminated in solution. The PMOs can by made by any means known in the art. The PMOs can be optimized for adsorption of TNT and similar compounds, however, PMO materials can be synthesized for adsorption of many materials, including, but not limited to, chemical warfare agents, pesticides, volatile organic compounds, or toxic industrial products. Optimization of the PMO materials is disclosed in Markowitz, et al., U.S. patent application Ser. No. 11/307, 286, filed Jan. 31, 2006, incorporated herein in full by reference. Potential applications include situations such as inline water treatment, environmental clean up, and exhaust stack filtering.

The optically active molecule is incorporated/embedded/bridged according to methods known in the art. When compared to previously synthesized PMO materials, the porphyrin-embedded materials have reduced specific surface area and pore volume. Porphyrin-free versions of the two PMOs were synthesized using the methods described and have BET surface areas from 400-500 $m^2/g$ and total pore volumes of 0.4-0.5 $cm^3/g$ as compared to 150 $m^2/g$ and 0.2 $cm^3/g$ obtained for the porphyrin-embedded versions. Those skilled in the art would understand that other methods of incorporation of the porphyrin into the PMO materials are possible, and that other methods to synthesize the PMO materials would work, and that variations of the template directed molecular imprinting process are also possible.

Having described the invention, the following example is given as a particular embodiment thereof and to demonstrate the practice and advantages thereof. It is understood that the examples are given by way of illustration and are not intended to limit the specification or the claims in any manner.

Meso-tetra(4-carboxyphenyl) porphine (CTPP) was obtained from Frontier Scientific, Logan, Utah. 1,4-bis(trimethoxysilylethyl)benzene was obtained from Gelest, Inc., Tullytown, Pa. Brij®76, NaOH, HCl, ethanol, p-cresol, and p-nitrophenol were purchased from Aldrich, Milwaukee, Wis. Materials were used as received unless otherwise indicated. Pure re-crystallized TNT was weighed on an analytic balance and dissolved in reagent grade acetonitrile to yield a final concentration of 1 mg/ml. The template molecule used to imprint the PMO material, decylamine trinitrobenzene (DATNB), was synthesized. The molecular structure of the DATNB consists of a 10-carbon chain (decane) bound to the amino group of 1-amino 2,4,6-trinitrobenzene.

The basic PMO preparation method used has been described in detail previously. see Burleigh, et al, Porous Polysilsesquioxanes for the Adsorption of Phenols, Environ Sci Technol. 36 (2002) 2515, incorporated herein in full by reference. For the non-imprinted material, Brij®76 was added to acidified water (20 g/L; ~2.4% HCl) while stirring. The mixture was covered and maintained at 50° C. for 12 hours after which a precursor, 1,4-bis(trimethoxysilylethyl) benzene, was added. After adding the precursor, the mixture was incubated for 2 additional hours to obtain gelation. The material was then aged and dried and the surfactant was removed. The synthesis of the imprinted material followed a variation of this protocol in which the template, DATNB, was added after the 12-hour period during which the surfactant (Brij®76) came to equilibrium. After 6 hours of incubation at 50° C. the solution was filtered using a 0.2 μm Teflon filter to remove excess template molecule. Further incubation over 3 hours was followed by addition of the precursor. For aging and drying and the surfactant removal, both imprinted and non-imprinted materials were handled identically. For synthesis of the porphyrin-embedded materials (imprinted and non-imprinted), porphyrin was added simultaneously with the precursor material. Porphyrin-embedded materials were not refluxed in deionized water prior to surfactant removal. Physiochemical properties were characterized via gas sorption using nitrogen gas as the adsorbate at 77 K with a Micromeritics ASAP 2010 (Norcross, Ga.). For the porphyrin-embedded, non-imprinted PMO material (PMO-A) the BET surface area was 157 $m^2/g$ with a total pore volume of 0.217 $cm^3/g$ and pore size of 54 Å (BJH adsorption). For the porphyrin-embedded, imprinted material (PMO-B), the BET surface area was 144 $m^2/g$ with a total pore volume of 0.221 $cm^3/g$ and pore size of 54 Å (BJH adsorption).

Samples of aromatic compounds were prepared as 10 ml aqueous solutions in Teflon capped glass test tubes at a concentration of 150 μM. Samples containing the analyte(s) under consideration and 10 mg of either PMO-A or PMO-B were placed on a rotary shaker outdoors in full sun for various time durations, as discussed below. Temperatures during these experiments were approximately 37° C. Analyte control solutions included identically prepared solutions at 150 μM with no PMO material which were either exposed to sunlight or protected from sunlight. Prepared analyte solutions containing one of the PMO materials were also used as dark control samples. Control solutions were exposed to temperature and handling procedures identical to those experienced by the samples. Solutions not exposed to sunlight were protected with aluminum foil wrapper. Immediately following the incubation period samples were filtered using 0.2 μm PTFE Acrodisc syringe filters (Gelman Sciences, Ann Arbor, Mich.).

Concentrations of the solutions used were measured by HPLC using EPA method 8330 on a Waters HPLC system with dual 510 pumps and a 717 autosampler coupled to a photodiode array detector. A 250 mm Altech Altima C18 column was employed with an isocratic 50:50 methaniol: water mobile phase. Difference method was used to determine changes in concentration. Absorbance spectra were collected in 96-well format using a Tecan XSafire monochromator-based microplate reader from 285 to 800 nm with 3 nm resolution. Fitting of data was accomplished in PSI-Plot (v7.5, Polysoftware, Int.) to a 98% confidence interval.

Figure 4:
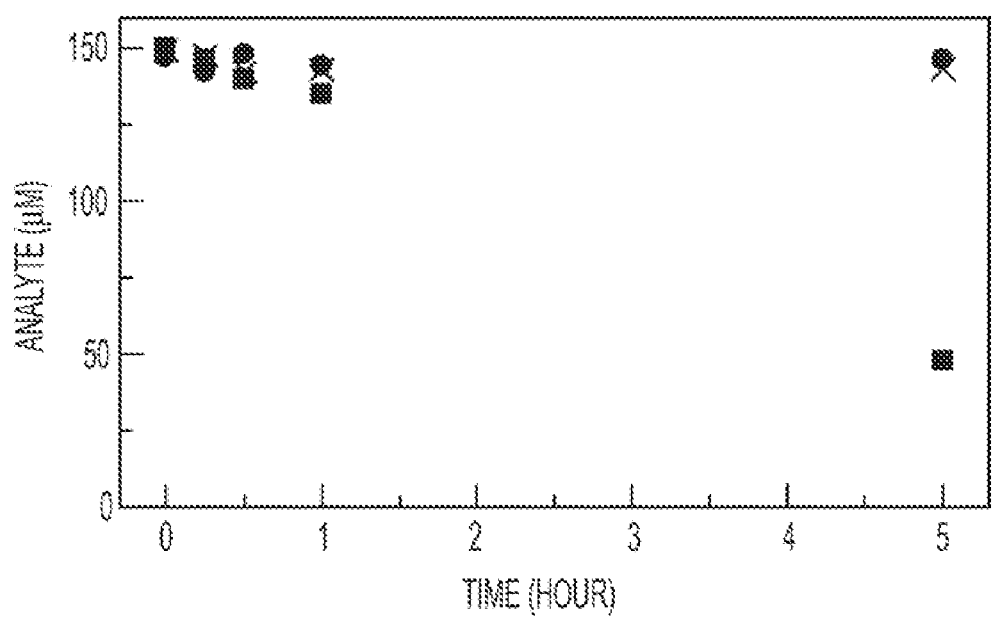
FIG. 4 shows results for single analyte aqueous solutions incubated over a 5 hour period under sunlight illumination in the absence of PMO materials.

Homogenous analyte solutions were used to determine baseline levels for changes in concentration under the experimental conditions. Aqueous analyte solutions prepared at 150 μM that were protected from sunlight showed no change in concentration over a five hour incubation period. Incubation of identical samples in sunlight showed a linear decrease in concentration over the five hour incubation period, as shown in FIG. 4, which shows results for single analyte aqueous solutions of p-cresol (●), p-nitrolphenol (x), and 2,4,6-trinitrotoluene (■) at 150 mM incubated over a 5 hour period under sunlight illumination in the absence of PMO materials. For p-cresol (pCR) and p-nitroplhenol (pNP), the total change in concentration was minimal compared to the initial sample concentration. For TNT, 32% of the original concentration remained after five hours sunlight exposure, as shown in FIG. 4. Nearly identical changes in concentration are observed when a ternary mixture containing pCR, pNP. and TNT (each analyte at 150 μM) is incubated in sun light.

The adsorption of the analytes under consideration by each of the porphyrin-embedded PMO materials was investigated to obtain baseline values for concentration changes in the analyte solutions. When 10 mg of PMO material (either A or B) was placed in a 150 μM aqueous Solution of analyte at 37° C., pNP and pCr adsorption reached equilibrium in less than 30 mins while that of TNT reached equilibrium after about 1 hour. Adsorption values are reported in Table 2 for samples incubated over a period of 5 hours. The PMO-B material showed approximately 20% less total adsorption for the three analytes than PMO-A when analytes were presented as single component solutions. TNT adsorption was not impacted by the presence of pNP and pCr in solution for either PMO material. For the non-imprinted PMO-A, a 20% reduction in adsorption of both pNP and pCr was observed in the ternary mixture. PMO-B showed a similar reduction in adsorption of pCr with a 35% reduction in pNP adsorption.

TABLE 2

Adsorption of analytes by PMO materials.

| | | PMO-A | | PMO-B | |
|---|---|---|---|---|---|
| | Analyte | μmol/g | nmol/m² | μmol/g | nmol/m² |
| Single Analyte | TNT | 127 | 809 | 102 | 708 |
| | pCr | 47 | 299 | 35 | 243 |
| | pNP | 34 | 217 | 28 | 194 |
| Ternary Mixture | TNT | 124 | 790 | 108 | 750 |
| | pCr | 39 | 248 | 29 | 201 |
| | pNP | 28 | 178 | 18 | 125 |

Figure 5A:
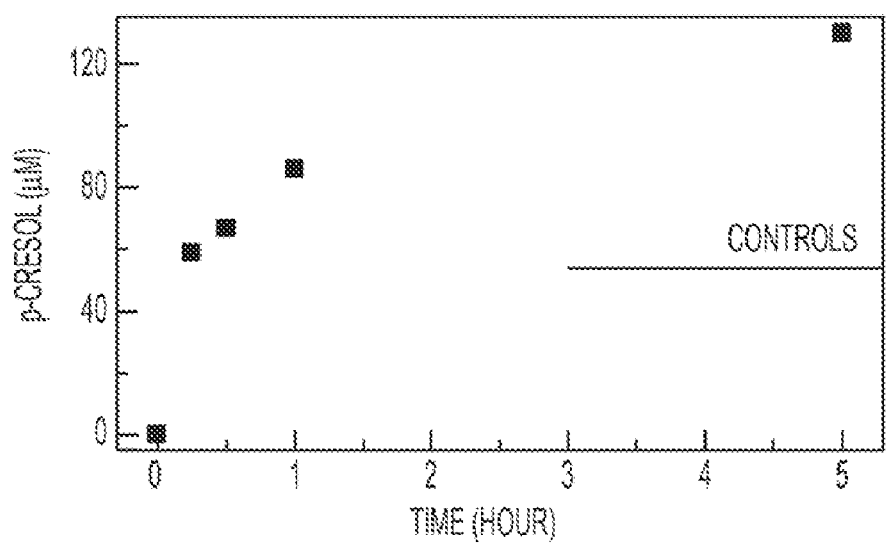
FIG. 5 shows the results of incubation of pCr with the two materials under sunlight illumination
Figure 5B:
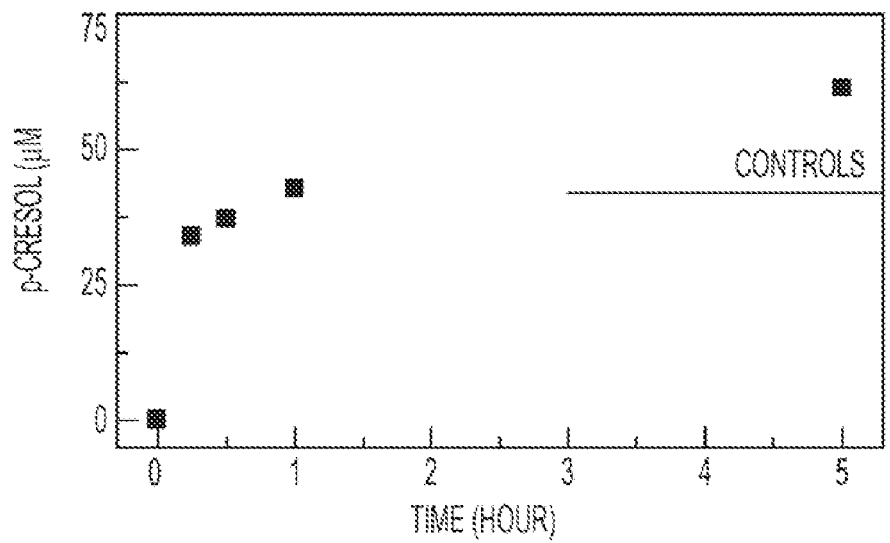

Illumination of single analyte solutions containing 150 μM pNP, pCr, or TNT and 10 mg of either PMO-A or PMO-B showed rates of change in concentration greater than that expected for the sum of uncatalyzed sunlight degradation of the analytes and adsorption onto the PMO material. FIG. 2 shows the results of incubation of pCr with the two materials under sunlight illumination. After one hour of incubation in sunlight with PMO-A, 888 nmol of pCr had been removed from the solution. This was well in excess of the total expected due to adsorption and catalyzed sunlight degradation in the absence of catalyst, 517 nmol. Though adsorption was expected to reach equilibrium after less than 1 hour, the concentration of pCr in solution continued to change throughout the five hour incubation as shown in FIG. 5. FIG. 5 shows p-Cresol removed from solution as a function of time when incubated with either PMO-A (A) or PMO-B (B) under sunlight illumination. Solid lines show the sum of the total change in concentration after five hours due to analyte adsorbed under dark conditions and sunlight illumination in the absence of PMO materials. Similarly, incubation under sunlight illumination increased the change in concentration for pNP when in the presence of either PMO-A or PMO-B as either single analyte or ternary solutions. Tables 3 and 4 summarize the increase in analyte removed from solution by the PMO materials as a result of sunlight exposure. Table 3 shows the change in analyte content (nmol) of single analyte aqueous samples after 1 and 5 hr incubation. Control value is the sum of changes from incubation of analyte alone with sunlight illumination and adsorption by the PMO, illuminated value is the change upon incubation of analyte and PMO with sunlight illumination.

TABLE 3

|  |  | PMO-A | | | PMO-B | | |
| --- | --- | --- | --- | --- | --- | --- | --- |
|  | Condition | pNP | pCr | TNT | pNP | pCr | TNT |
| Change after 1 hr | Control | 404 | 517 | 1350 | 349 | 411 | 1210 |
|  | Illuminated | 480 | 888 | 1440 | 450 | 456 | 1390 |
| Change after 5 hr | Control | 410 | 528 | 2290 | 350 | 408 | 2140 |
|  | Illuminated | 748 | 1330 | 1500 | 688 | 642 | 1490 |

Table 4 shows the change in analyte content (nmol) of ternary analyte mixtures after 5 hr incubation. Control value is the sum of changes from incubation of analyte alone with sunlight illumination and adsorption by the PMO, illuminated value is the change upon incubation of analyte and PMO with sunlight illumination.

TABLE 4

|  |  | PMO-A | | | PMO-B | | |
| --- | --- | --- | --- | --- | --- | --- | --- |
|  | Condition | pNP | pCr | TNT | pNP | pCr | TNT |
| Change after 1 hr | Control | 344 | 407 | 1320 | 248 | 305 | 1190 |
|  | Illuminated | 442 | 391 | 1360 | 370 | 359 | 1270 |
| Change after 5 hr | Control | 348 | 438 | 1260 | 252 | 346 | 2102 |
|  | Illuminated | 705 | 499 | 1480 | 541 | 353 | 1477 |

The potential of two porphyrin-embedded periodic mesoporous organosilica materials to catalyze sunlight driven degradation of cyclic organics in aqueous solution was investigated. The impact of template directed molecular imprinting was investigated for its potential to generate materials with enhanced TNT selectivity. The change in concentration of the analytes pNP and pCr upon incubation with the PMO materials under sunlight illumination exceeded that expected based on the uncatalyzed photoconversion and adsorption values. This indicates the involvement of the PMO materials in a sunlight stimulated reaction. While the pNP and pCr losses clearly illustrate the effectiveness of the porphyrin-embedded material to enhance the sunlight driven degradation of the compounds, the TNT results are less than convincing. This is likely attributable to the higher affinity of the PMO materials for this analyte and the relatively high uncatalyzed photoconversion rate. Experiments were also conducted using ternary mixtures of the analytes (See Table 4) though analysis is complicated by strong TNT adsorption and fast solution photoconversion. The conversion of pCr is dramatically reduced for both PMO materials when analytes are presented as mixtures while pNP conversion is impacted only for PMO-B. Improved selectivity of the materials upon imprinting would explain this difference though the experiment doesn't exclude other possibilities.

Though TNT samples are initially clear, a pink color develops quickly upon exposure to sunlight in aqueous solution. This rapid conversion of TNT in the presence of sunlight and water makes the changes in concentration upon incubation with the PMO materials difficult to analyze. If end-point analysis is used after 5 hour incubation, the results are inconclusive with changes in the TNT concentration attributable to only uncatalyzed photoconversion and adsorption by the PMO materials. Even at the 1 hour time point, the advantage of incubation with the PMO materials under sunlight illumination is arguable. The pink color observed to develop in the TNT samples is attributable to 1,3,5-trinitrobenzene (TNB), a product of TNT photoconiversion. For the HPLC method employed, TNB is eluted with the void volume of the sample making quantification of its presence impossible. In order to attempt to address this difficulty, absorbance values for the samples at 435 nm were measured. Based on these absorbance values, the TNB concentration for samples increases more rapidly than that of control samples containing no PMO when both are illuminated by sunlight. This data indicates the potential involvement of the PMO in enhancement of sunlight catalyzed degradation of TNT. The final concentration of TNB in the PMO-B containing samples after illumination (based on 435 nm absorbance) is 37% less than that of illuminated samples containing TNT and no PMO, however, drawing conclusions based on this information is difficult due to the likely adsorption of TNB onto the PMO materials.

The two PMO materials vary in that synthesis of PMO-B involved the use of template directed molecular imprinting (TDMI) against decylaminetrinitrobenzene, a TNT analog. The synthesis here varies from the previously employed methods in that a porphyrin has been incorporated into the PMO material. While TDMI should tend to make the structure of the material more homogeneous, incorporation of the porphyrin can conceivably disrupt the structure. The TDMI process was used in an attempt to improve the selectivity of the PMO material for TNT. Though a small improvement in selectivity (noted as a decrease in pNP adsorption from the ternary mixture for PMO-B) was obtained, it was at the expense of total adsorption of the target, TNT. Experiments using a mixture of analytes demonstrate that both of these less than optimal materials still achieve some degree of selectivity for TNT over pNP and pCr. As seen in Table 1, the adsorption of TNT is unaffected by the presence of pCr and pNP in solution.

Obviously, many modifications and variations of the present invention are possible in light of the above teachings. It is therefore to be understood that, within the scope of the appended claims, the invention may be practiced otherwise than as specifically described.

What is claimed as new and desired to be protected by Letters Patent of the United States is:

1. A photo-decontamination catalyst comprising:
   a periodic mesoporous organosilica; and
   an optically active molecule; said optically active molecule being incorporated into said periodic mesoporous organosilica, wherein said periodic mesoporous organosilica is configured to orient a target molecule with respect to said optically active molecule.

2. The catalyst of claim 1 wherein said optically active molecule is a fluorophore or chromophore.

3. The catalyst of claim 1 wherein said optically active molecule is selected from the group consisting of porphyrins and phthalocyanines.

4. The catalyst of claim 2 wherein said chromophore or fluorophore is selected from fluorescein and fluorescein derivatives and analogues, indocyanine green, rhodamine, triphenylmethines, polymethines, cyanines, phalocyanines, naphthocyanines, merocyanines, lanthanide complexes or cryptates, fullerenes, oxatellurazoles, LaJolla blue, porphyrins and porphyrin analogues and natural chromophores/fluorophores such as chlorophyll, carotenoids, flavonoids, bilins, phytochrome, phycobilins, phycoerythrin, phycocyanines, retinoic acid and analogues such as retinoins and retinates.

5. The catalyst of claim 1 wherein said periodic mesoporous organosilica is a molecularly imprinted periodic mesoporous organosilica.

6. The catalyst of claim 5 wherein said molecularly imprinted periodic mesoporous organosilica is a template directed molecularly imprinted periodic mesoporous organosilica.

7. The catalyst of claim 1 wherein the target molecule is TNT, TNT-derivatives, a chemical warfare agent, a pesticide, or volatile organic compound.

8. A method for photo-decontaminating a sample containing a target molecule comprising:
   providing a periodic mesoporous organosilica incorporating an optically active molecule, wherein said periodic mesoporous organosilica is configured to orient a target molecule with respect to said optically active molecule;
   providing a sample containing a target molecule;
   exposing said periodic mesoporous organosilica to said sample containing a target molecule, wherein said target molecule is adsorbed into said periodic mesoporous organosilica;
   providing a light source; and
   exposing said periodic mesoporous organosilica to said light source, wherein said optically active molecule catalyzes the decontamination of said target molecule in the presence of said light source.

9. The method of claim 8 wherein said optically active molecule is a fluorophore or chromophore.

10. The method of claim 8 wherein said optically active molecule is selected from the group consisting of porphyrins and phthalocyanines.

11. The method of claim 9 wherein said chromophore or fluorophore is selected from fluorescein and fluorescein derivatives and analogues, indocyanine green, rhodamine, triphenylmethines, polymethines, cyanines, phalocyanines, naphthocyanines, merocyanines, lanthanide complexes or cryptates, fullerenes, oxatellurazoles, LaJolla blue, porphyrins and porphyrin analogues and natural chromophores/fluorophores such as chlorophyll, carotenoids, flavonoids, bilins, phytochrome, phycobilins, phycoerythrin, phycocyanines, retinoic acid and analogues such as retinoins and retinates.

12. The method of claim 8 wherein said periodic mesoporous organosilica is a molecularly imprinted periodic mesoporous organosilica.

13. The method of claim 12 wherein said molecularly imprinted periodic mesoporous organosilica is a template directed molecularly imprinted periodic mesoporous organosilica.

14. The method of claim 8 wherein the target molecule is TNT, TNT-derivatives, chemical warfare agents, pesticides, or volatile organic compounds.

15. The method of claim 8 wherein said light source covers the blue to red regions of the visible spectrum.

16. The method of claim 15 wherein said light source is sunlight.

* * * * *